(12) United States Patent
Morita et al.

(10) Patent No.: US 6,461,597 B1
(45) Date of Patent: Oct. 8, 2002

(54) METHOD OF TREATING HAIR OR SKIN

(75) Inventors: Yoshitsugu Morita, Chiba Prefecture (JP); Kazuo Kobayashi, Chiba Prefecture (JP); Ozaki Masaru, Chiba Prefecture (JP)

(73) Assignee: Dow Corning Toray Silicone Co., LTD., Tokyo (JP)

( * ) Notice: Subject to any disclaimer, the term of this patent is extended or adjusted under 35 U.S.C. 154(b) by 0 days.

(21) Appl. No.: 09/707,512

(22) Filed: Nov. 7, 2000

(30) Foreign Application Priority Data

Nov. 16, 1999 (JP) ............................... 11-324840

(51) Int. Cl.[7] .................. A61K 7/06; A61K 7/00; A61K 9/14; A61K 31/695; C08K 5/54
(52) U.S. Cl. .................. 424/70.1; 424/401; 424/484; 424/485; 424/486; 424/70.11; 424/70.12; 424/70.16; 424/DIG. 2; 514/63; 514/772.3; 514/880; 514/951; 524/731; 524/267
(58) Field of Search .................. 404/70.1, 401, 404/484, 485, 486, 70.11, 70.12, 70.16, DIG. 2; 514/63, 772.3, 880, 951; 524/731, 207

(56) References Cited

U.S. PATENT DOCUMENTS

| | | | |
|---|---|---|---|
| 4,980,167 A | 12/1990 | Harashima et al. | 424/401 |
| 4,987,169 A * | 1/1991 | Kuwata et al. | 524/267 |
| 5,154,849 A | 10/1992 | Visscher et al. | 252/174.15 |
| 5,889,108 A * | 3/1999 | Zhang | 424/70.11 |
| 5,969,035 A * | 10/1999 | Meinhardt et al. | 524/731 |

FOREIGN PATENT DOCUMENTS

| | | |
|---|---|---|
| EP | 0 295886 | 12/1988 |
| JP | 61-194009 | 8/1986 |
| JP | 1-165509 | 6/1989 |
| JP | 1-190757 | 7/1989 |
| JP | 1-207354 | 8/1989 |
| JP | 2-172906 | 7/1990 |
| JP | 3-79669 | 4/1991 |
| JP | 3-271211 | 12/1991 |
| JP | 5-139932 | 6/1993 |
| JP | 5-262987 | 10/1993 |
| JP | 7-258027 | 10/1995 |
| JP | 7-267820 | 10/1995 |
| JP | 7-330537 | 12/1995 |
| JP | 10-36228 | 2/1998 |

* cited by examiner

*Primary Examiner*—Frederick Krass
*Assistant Examiner*—Clinton Ostrup
(74) *Attorney, Agent, or Firm*—Jim L. De Cesare

(57) ABSTRACT

A cosmetic consists of a cosmetic raw material in the form of an emulsion of silicone or organic oil containing crosslinked particles mixed with other cosmetic raw materials. Its touch on fingers and skin is good, spreading and feel during use are good, and it can also prevent unruly hair, stray hair, and tangling of hair, so hair can easily be arranged. It imparts a fresh, dry feeling without any stickiness. The cosmetic raw material consists of the silicone or organic oil emulsion containing crosslinked particles with a mean particle diameter of 0.05 to 100 $\mu$m. Crosslinking is obtained by an hydrosilylation of liquid crosslinkable compositions consisting of (A) organic compounds with at least two aliphatic unsaturated bonds per molecule, (B) silicon containing organic compounds with at least two hydrogen atoms bonded to silicon atoms in each molecule, and (C) hydrosilylation reaction catalysts. The resulting crosslinked particles are contained in the droplets of the silicone oil or the organic oil which have mean particle sizes of 0.1 to 500 $\mu$m, and which droplets are in turn dispersed in water.

6 Claims, No Drawings

METHOD OF TREATING HAIR OR SKIN

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

1. Field of the Invention

This invention relates to a cosmetic raw material, a cosmetic, and a cosmetic manufacturing method. More specifically, the invention relates to [a] a cosmetic raw material that is capable of uniformly dispersing a silicone or organic oil and crosslinked particles in a cosmetic; [b] a cosmetic [i] which consists of cosmetic raw material [a] and other cosmetic raw materials, [ii] in which a silicone oil or organic oil and crosslinked particles are uniformly dispersed, [iii] in which the touch on fingers and skin, spreading and feeling of use are good, [iv] which prevents unruly hair, stray hair, and tangling hair so that hair can easily be arranged, and [v] which can impart a fresh, dry feeling without any stickiness; and [c] a method for efficient manufacture of such cosmetic.

2. Background of the Invention

The use of silicone oils, organic oils, and crosslinked silicone particles as cosmetic raw materials for improving the feeling and slip properties of cosmetics on the skin, or for improving the feeling of use and slip properties of hair cosmetics, is known. The use of silicone oils or organic oils with crosslinked silicone parts in such applications is also known.

Examples of cosmetics containing silicone oils and crosslinked silicone particles include cosmetics which contain crosslinked silicone particles that have a three dimensional network structure and high viscosity or low-viscosity silicone oils, as shown in Japanese Patent Application Kokai No. Hei 1-165509, and Japanese Patent Application Kokai No. Hei-1-190757. Cosmetics which contain the crosslinked product of a hydrosilylation crosslinkable silicone composition and a low viscosity silicone oil are shown in Japanese Patent Application Kokai No. Hei 1-207354. A cosmetic which contains a silicone oil emulsion consisting of a crosslinked silicone product, a low viscosity silicone oil, a polyoxysilane modified silicone type surfactant and water, is shown in Japanese Patent Application Kokai No. Hei 3-79669. A foundation cosmetic material which contains a silicone oil emulsion of a low viscosity silicone oil and a silicone that is solid at room temperature, is shown in Japanese Patent Application Kokai No. Hei 3-271211. A skin cleansing agent which contains a silicone rubber and a silicone oil, is shown in Japanese Patent Application Kokai No. Hei 6-502646/U.S. Pat. No. 5,154,849, Oct. 13, 1992. A cosmetic consisting of a high-molecular weight silicone and a silicone rubber, is shown in Japanese Patent Application Kokai No. Hei 7-330537.

Hair cosmetics that contain silicone oils and crosslinked silicone particles are shown in Japanese Patent Application Kokai No. Hei 2-172906; Japanese Patent Application Kokai No. Hei 5-139932; and Japanese Patent Application Kokai No. Hei 10-36228. Hair cosmetics containing crosslinked silicone particles that contain a silicone oil are shown in Japanese Patent Application Kokai No. Hei 2-243612/U.S. Pat. No. 4,980,167, Dec. 25, 1990; and Japanese Patent Application Kokai No. Hei 5-262987.

Cosmetics that contain organic oils and crosslinked silicone particles are shown in Japanese Patent Application Kokai No. Sho 61-194009; Japanese Patent Application Kokai No. Sho 63-313710/EP 295886, Dec. 21, 1988; Japanese Patent Application Kokai No. Hei 7-258027; and Japanese Patent Application Kokai No. Hei 7-267820.

However, in these cosmetics, the silicone oils or organic oils and the crosslinked silicone particles used as raw materials are combined with other cosmetic raw materials. As a result, the crosslinked silicone particles are not sufficiently dispersed in the cosmetics. Furthermore, the silicone oils or organic oils used have a poor affinity for the crosslinked silicone particles, so that the intrinsic characteristics of the particles cannot be sufficiently exhibited. For any water based cosmetic, in particular, a sufficient shear force cannot be applied when the silicone oils or organic oils and the crosslinked silicone particles are dispersed in other cosmetic raw materials, and as a result, the stability of the cosmetics is insufficient, and the feel provided when the cosmetics are used is generally poor.

In the case of a hair cosmetic in which silicone oils or organic oils and the crosslinked silicone particles are used as cosmetic raw materials, the crosslinked silicone particles are not sufficiently dispersed in the hair cosmetic. Moreover, the affinity of the silicone oils or organic oils for the crosslinked silicone particles is poor, so that the intrinsic characteristics of the crosslinked silicone particles cannot be sufficiently exhibited. For water based hair cosmetics in particular, a sufficient shear force cannot be applied when the silicone oils or organic oils and the crosslinked silicone particles are dispersed in other hair cosmetic raw materials. As a result, the stability of the hair cosmetics is insufficient, and the feel experienced when the hair cosmetic is used is generally poor.

BRIEF SUMMARY OF THE INVENTION

The object of this invention is to provide [a] a cosmetic raw material capable of uniformly dispersing a silicone or organic oil and crosslinked particles in a cosmetic; [b] a cosmetic [i] which consists of such cosmetic raw material and other cosmetic raw materials, [ii] in which a silicone oil or organic oil and crosslinked particles are uniformly dispersed, [iii] in which the touch on fingers and skin, the spread of the cosmetic and the feeling of use are good, [iv] which prevents unruly hair, stray hair and tangling of hair, so hair can easily be arranged, and [v] which can impart a fresh, dry feeling without any stickiness; and [c] a method for the efficient manufacture of such cosmetic.

These and other features of the invention will become apparent from a consideration of the detailed description.

BRIEF DESCRIPTION OF THE SEVERAL VIEWS OF THE DRAWING

Not applicable.

DETAILED DESCRIPTION OF THE INVENTION

The cosmetic raw material of the invention consists of a silicone oil or an organic oil emulsion containing crosslinked particles with a mean particle diameter of 0.05 to 100 $\mu$m. The particles are crosslinked by a hydrosilylation reaction of a liquid crosslinkable composition consisting of (A) an organic compound having at least two aliphatic unsaturated bonds per molecule, (B) a silicon containing organic compound having at least two hydrogen atoms bonded to silicon atoms in each molecule, (C) a hydrosilylation reaction catalyst, and optionally (D) an organopolysiloxane having at least one alkenyl group per molecule. The crosslinked particles are contained in droplets of the silicone oil or in droplets of the organic oil. The droplets have a mean particle size of 0.1 to 500 $\mu$m, and the droplets are dispersed in water. The particle diameter of the crosslinked particles is smaller than the particle diameter of the droplets of the silicone oil or the droplets of the organic oil.

According to one embodiment of the invention, the cosmetic raw material consists of an oil composition in which the crosslinked particles are dispersed in the silicone oil or in the organic oil, and the oil composition is obtained by removing water from the emulsion.

In another embodiment, the cosmetic of the invention consists of the cosmetic raw material which comprises the emulsion combined with other cosmetic raw materials.

In a further embodiment, the cosmetic of the invention consists of the cosmetic raw material which comprises the oil composition combined with other cosmetic raw materials.

In yet another embodiment, the cosmetic of the invention is prepared according to a method in which the cosmetic raw material consisting of the emulsion is combined with other cosmetic raw materials.

WORKING EMBODIMENTS OF THE INVENTION

First, the cosmetic raw material of the invention will be described in detail.

The cosmetic raw material is characterized by the fact that it consists of an emulsion of a silicone oil or an organic oil in which crosslinked particles are contained in droplets of the silicone oil or the organic oil which are in turn dispersed in water. In the emulsion, there are no restrictions on the type of silicone oil that can be used. Some examples are silicone oils with molecular structures which are linear, linear with some branching, cyclic, or those having a branched chain structure. Silicone oils with linear or cyclic molecular structures are preferred.

The silicone oil should be one that does not participate in the hydrosilylation reaction which forms the crosslinked particles. Such silicone oils include dimethylpolysiloxanes in which both ends of the molecular chains are closed by trimethylsiloxy groups; methylphenylpolysiloxanes in which both ends of the molecular chains are closed by trimethylsiloxy groups; dimethylsiloxane/methylphenylsiloxane copolymers in which both ends of the molecular chains are closed by trimethylsiloxy groups; dimethylsiloxane/methyl(3,3,3-trifluoropropyl) siloxane copolymers in which both ends of the molecular chains are closed by trimethylsiloxy groups; cyclic dimethylsiloxanes; cyclic methylphenylsiloxanes; and silicone oils containing organic groups such as polyether groups, long chain alkyl groups, epoxy groups, carboxy groups, ester groups, amido groups, amino groups, and mercapto groups.

In the emulsion, there are no restrictions on the types of organic oils that can be used. However, organic oils that are compatible with the liquid form of the crosslinkable composition used to form the crosslinked particles are desirable. These organic oils should be aliphatic oils or aromatic oils that have a linear molecular structure, a linear structure with some branching, a cyclic structure, or a branched chain structure. Organic oils with a linear or a cyclic molecular structure are preferred. The organic oils can be volatile.

Some examples of organic oils that do not participate in the hydrosilylation reaction that forms the crosslinked particles are alkanes such as hexane, heptane, paraffin and isoparaffin; aromatic compounds such as toluene and xylene; ketones such as methyl isobutyl ketone; alcohols such as undecyl alcohol; ethers such as dibutyl ether; and esters such as isopropyl laurate and isopropyl palmitate. Volatile alkanes are especially desirable.

The silicone oils and organic oils may be used in combination one with the other, or other components can be dissolved in the oils. When volatile silicone oils or organic oils are used, a mixture of crosslinked particles and other components can be dissolved in the silicone oil or the organic oil, or the crosslinked particles containing other components can be prepared by removing water and the volatile silicone oil or organic oil from the emulsion of the silicone oil or organic oil. There are no restrictions on the other types of components that can be dissolved in the silicone oils or organic oils provided the components are soluble in the silicone oils or organic oils.

Some examples of other components that can be used are organosilicon compounds such as silicone resins that are solid at room temperature, and silicone oils that exhibit a rubbery state at room temperature; waxes such as carnauba wax, candelilla wax, Japan wax, spermaceti wax, montan wax, beeswax, and lanolin; liquid paraffin, isoparaffin, hexyl laurate, isopropyl myristate, myristyl myristate, cetyl myristate, 2-octyldecyl myristate, isopropyl palmitate, 2-ethylhexyl palmitate, butyl stearate, decyl oleate, 2-octyldecyl oleate, myristyl lactate, cetyl lactate, lanolin acetate, stearyl alcohol, cetostearyl alcohol, oleyl alcohol; fats and oils such as avocado oil, almond oil, olive oil, cacao oil, jojoba oil, sesame oil, safflower oil, soybean oil, camellia oil, squalane, persic oil, castor oil, mink oil, cottonseed oil, coconut oil, egg yolk oil, and lard; glycol ester oils such as polypropylene glycol monooleate and neopentyl glycol 2-ethylhexanoate; polyhydric alcohol ester oils such as isostearic acid triglyceride and coconut oil fatty acid triglycerides; and polyoxyalkylene ether oils such as polyoxyethylene lauryl ether and polyoxypropylene cetyl ether.

In the emulsion, there are no restrictions on the viscosity of the silicone oil or the organic oil. However, it is desirable that the viscosity at 25° C. be in the range of 1 to 100,000,000 mPa.s. A viscosity in the range of 2 to 10,000,000 mPa.s is especially desirable. The mean particle size of droplets of the silicone oil or the organic oil in the emulsion is 0.1 to 500 $\mu$m, preferably 0.2 to 500 $\mu$m, more preferably 0.5 to 500 $\mu$m, and most preferably 0.5 to 200 $\mu$m. It is difficult to manufacture an emulsion in which the mean particle size of the droplets is smaller than the lower limit of the range, and when the mean particle size of the droplets exceeds the upper limit of the range, the stability of the emulsion tends to decrease.

The crosslinked particles used in the emulsion are obtained by using a hydrosilylation reaction to crosslink a liquid form of a crosslinkable composition consisting of (A) an organic compound that has at least two aliphatic unsaturated bonds per molecule, (B) a silicon containing organic compound that has at least two hydrogen atoms bonded to silicon atoms in each molecule, (C) a hydrosilylation reaction catalyst, and optionally (D) an organopolysiloxane that has at least one alkenyl group per molecule.

The organic compound of component (A) should be a compound having at least two aliphatic unsaturated bonds per molecule. Some examples of groups having aliphatic unsaturated bonds in component (A) include molecular chain terminal groups and molecular chain side chain groups, among which are alkenyl groups such as vinyl groups, allyl groups, butenyl groups, and pentenyl groups; alkynyl groups such as ethynyl groups; cyclic unsaturated groups such as norbornene groups and dicyclopentadienyl groups; and groups contained within molecular chains among which are enylene groups such as vinylene groups and propenylene groups. The preferred groups are molecular chain terminal groups or molecular chain side chain groups such as vinyl groups or allyl groups.

There are no restrictions on the physical state of component (A), and it may be a solid or liquid. Liquid components are preferred. If component (A) is used as a solid, it is necessary to dissolve component (A) in another component beforehand, or dissolve component (A) in an organic solvent prior to its use. There are also no restrictions on the molecular weight of component (A). However, it is desirable that the average molecular weight of component (A) be in the range of 50 to 50,000.

Some examples of compounds that can be used as component (A) include dienes such as pentadiene, hexadiene, heptadiene, octadiene, nonadiene, cyclopentadiene, and cyclooctadiene; aromatic dienes such as divinylbenzene; ethers such as diallyl ether, triethylene glycol divinyl ether, cyclohexane dimethanol divinyl ether and 1,2-divinylglycol; and esters such as diallyl isophthalate, diallyl phthalate, diallylterephthalic acid, diallyl maleate, and triallyl trimellitate. Component (A) can also be an oligomer obtained by polymerizing these types of compounds.

Other oligomers which can be used as component (A) include oligomers with at least two aliphatic unsaturated bonds per molecule obtained by polymerizing olefins such as ethylene, propylene, butene, isobutene, pentene, and hexane; oligomers obtained by polymerizing alkenyl group containing acrylic monomers such as allyl(meth)acrylate, butenyl(meth)acrylate, methylbutenyl(meth)acrylate, methylpropenyl(meth)acrylate, heptenyl(meth)acrylate, and hexenyl(meth)acrylate, or oligomers obtained by copolymerizing such acrylic monomers with monomers such as methyl(meth)acrylate, ethyl(meth)acrylate, butyl(meth) acrylate, ethylhexyl(meth)acrylate, lauryl(meth)acrylate, styrene, α-methylstyrene, maleic acid, vinyl acetate or allyl acetate.

Some further examples of component (A) include oligomers obtained by a process in which oligomers obtained by copolymerizing hydroxy group containing acrylic monomers such as 2-hydroxyethyl(meth)acrylate, 2-hydroxypropyl(meth)acrylate, or 4-hydroxybutyl(meth) acrylate, with (i) alkenyl isocyanates such as allyl isocyanate, (meth)acryloyl isocyanate, or 2-isocyanatoethyl (meth)acrylate, or with (ii) alkenyl-group containing carboxylic acid anhydrides such as itaconic anhydride, maleic anhydride or tetrahydrophthalic anhydride.

Yet more examples of component (A) are oligomers obtained by polymerizing isocyanate group containing monomers such as (meth)acryloyl isocyanate or ethyl(meth) acrylate 2-isocyanate, or oligomers obtained by copolymerizing such isocyanate group containing monomers with alkenyl alcohols such as allyl alcohol, butenol, 2-(allyloxy) ethanol, glycerol diallyl ether, cyclohexene methanol, methylbutenol, or oleyl alcohol.

Still more examples of component (A) include oligomers obtained by polymerizing carboxy group containing monomers such as (meth)acrylic acid, itaconic acid, or maleic acid, or oligomers obtained by copolymerizing such carboxy group containing monomers with alkenyl-group containing epoxy compounds such as glycidyl(meth)acrylate, or allylglycidyl ether.

Component (A) can be a polyether obtained by ring opening polymerization of allyl glycidyl ether using ethylene glycol as an initiator, or a polyether obtained by ring opening polymerization of vinylcyclohexane-1,2-epoxide using butanol, allyl alcohol, or propargyl alcohol, as an initiator.

Component (A) can also be an alkenyl group containing polyester obtained by reacting alkenyl alcohols, polyhydric alcohols such as ethylene glycol, propylene glycol, 1,6-hexanediol, diethylene glycol, neopentyl glycol, neopentyl glycol hydroxypivalate, or trimethylolpropane, with polybasic acids such as phthalic anhydride, isophthalic acid, terephthalic acid, adipic acid, azelaic acid or trimellitic acid.

Component (A) is most preferably a diene, a diene oligomer, or a polyether.

Silicon containing organic compounds used as component (B) should have at least two hydrogen atoms bonded to silicon atoms in each molecule. There are no restrictions on the viscosity of component (B). However, it is desirable that the viscosity at 25° C. be in the range of 1 to 100,000 mPa.s, and a viscosity in the range of 1 to 10,000 mPa.s is especially desirable. Examples of silicon containing organic compounds that can be used as component (B) include organohydridopolysiloxanes, and organic polymers that have diorganohydridosilyl groups, but it is preferred that organohydridopolysiloxanes be used.

Organohydridopolysiloxanes used as component (B) may have a linear molecular structure, a branched structure, a cyclic structure, a network structure, or a linear structure with some branching. Some examples of compounds useful as component (B) include methylhydridopolysiloxanes in which both ends of the molecular chain are closed by trimethylsiloxy groups; dimethylsiloxane/methylhydridosiloxane copolymers in which both ends of the molecular chain are closed by trimethylsiloxy groups; dimethylsiloxane/methylhydridosiloxane/methylphenylsiloxane copolymers in which both ends of the molecular chain are closed by trimethylsiloxy groups; dimethylpolysiloxanes in which both ends of the molecular chain are closed by dimethylhydridosiloxy groups; dimethylsiloxane/methylphenylsiloxane copolymers in which both ends of the molecular chain are closed by dimethylhydridosiloxy groups; and methylphenylpolysiloxanes in which both ends of the molecular chain are closed by dimethylhydridosiloxy groups.

Component (B) can also be an organopolysiloxane copolymer consisting of siloxane units of the formula $R_3SiO_{1/2}$, siloxane units of the formula $R_2HSiO_{1/2}$, and siloxane units of the formula $SiO_{4/2}$; an organopolysiloxane copolymer consisting of siloxane units of the formula $R_2HSiO_{1/2}$, and siloxane units of the formula $SiO_{4/2}$; an organopolysiloxane copolymer consisting of siloxane units of the formula $RHSiO_{2/2}$, and siloxane units of the formula $RSiO_{3/2}$ or $HSiO_{3/2}$; or component (B) can be a mixture consisting of two or more of such organopolysiloxanes. R in these formulas indicates a monovalent hydrocarbon group other than an alkenyl group. Some examples of such groups include alkyl groups such as methyl groups, ethyl groups, propyl groups, butyl groups, pentyl groups, hexyl groups, and heptyl groups; aryl groups such as phenyl groups, tolyl groups, xylyl groups, and naphthyl groups; aralkyl groups such as benzyl groups, and phenethyl groups; and halogenated alkyl groups such as chloromethyl groups, 3-chloropropyl groups, and 3,3,3-trifluoropropyl groups.

Some examples of compounds that can be used as component (B) include oligomers obtained by copolymerizing dimethylhydridosilyl group containing acrylic monomers such as dimethylhydridosilyl(meth)acrylate or dimethylhydridosilylpropyl(meth)acrylate, with monomers such as methyl(meth)acrylate, ethyl(meth)acrylate, butyl(meth)acrylate, ethylhexyl(meth)acrylate, lauryl(meth)acrylate, styrene, α-methylstyrene, maleic acid, vinyl acetate, or allyl acetate.

In the crosslinkable composition, the content of component (B) should be 0.1 to 500 parts by weight per 100 parts by weight of component (A), or per 100 parts by weight of the total of components (A) and (D). A content in the range of 0.5 to 500 parts by weight is even more desirable, and a content in the range of 1 to 100 parts by weight is especially preferred. If the content of component (B) is less than the lower limit of the range, there is a danger that sufficient crosslinking will not occur. If the content of component (B) exceeds the upper limit of the range, there is a danger that excess hydrogen atoms bonded to silicon atoms will generated hydrogen gas.

Component (C) is an hydrosilylation reaction catalyst used to cause crosslinking by promoting the hydrosilylation reaction of the crosslinkable composition. Some examples of catalysts that can be used as component (C) include platinum type catalysts, rhodium type catalysts, and palladium type catalysts. Preferably, a platinum catalyst is used. Some specific examples of platinum catalysts include finely powdered silica supported on platinum, finely powdered carbon supported on platinum, chloroplatinic acid, alcohol solutions of chloroplatinic acid, olefin complexes of platinum, alkenylsiloxane complexes of platinum, and carbonyl complexes of platinum.

In the crosslinkable composition, there are no restrictions on the content of component (C) provided the amount is sufficient to promote hydrosilylation of the crosslinkable composition. When a platinum type catalyst is used as component (C), it is desirable that the amount of platinum metal in component (C) be $1\times10^{-7}$ to $1\times10^{-3}$ parts by weight per 100 parts by weight of the total of components (A) and (B), or per 100 parts by weight of the total of components (A), (B), and (D). If the content of component (C) is less than the lower limit of the range, there is a danger that crosslinking will not proceed to a sufficient degree. If the content exceeds the upper limit of the range, there is no additional effect and a large content is therefore not economical.

While organopolysiloxane component (D) is an optional component in the crosslinkable composition, when it is included, it should be one containing at least one alkenyl group per molecule. Component (D) is used to provide the resulting material with pliability and rubber elasticity by improving the affinity of the crosslinked particles for the silicone oil. It is preferred that component (D) be an organopolysiloxane having at least two alkenyl groups per molecule. Some examples of alkenyl groups in component (D) include vinyl groups, allyl groups, butenyl groups, pentenyl groups, and hexenyl groups, and vinyl groups are preferred. In addition, groups other than alkenyl groups can be bonded to silicon atoms in component (D) among which are monovalent hydrocarbon groups including alkyl groups such as methyl groups, ethyl groups, propyl groups, and butyl groups; cycloalkyl groups such as cyclopentyl groups and cyclohexyl groups; aryl groups such as phenyl groups, tolyl groups, and xylyl groups: aralkyl groups such as benzyl groups, phenethyl groups, and 3-phenylpropyl groups; and halogenated hydrocarbon groups such as 3-chloropropyl groups and 3,3,3-trifluoropropyl groups. The molecular structure of component (D) may be linear, branched, cyclic, in a network form, or linear with some branching. A linear molecular structure is preferred. There are no restrictions on the viscosity of component (D), but it is desirable that the viscosity at 25° C. be 20 to 100,000 mPa.s, and a viscosity of 20 to 10,000 mPa.s is especially preferred.

Some specific examples of compounds which can be used as component (D) include dimethylsiloxane/methylvinylsiloxane copolymers in which both ends of the molecular chain are closed by trimethylsiloxy groups; methylvinylpolysiloxanes in which both ends of the molecular chain are closed by trimethylsiloxy groups; dimethylsiloxane/methylvinylsiloxane/methylphenylsiloxane copolymers in which both ends of the molecular chain are closed by trimethylsiloxy groups; dimethylpolysiloxanes in which both ends of the molecular chain are closed by dimethylvinylsiloxy groups; methylvinylpolysiloxanes in which both ends of the molecular chain are closed by dimethylvinylsiloxy groups; dimethylsiloxane/methylvinylsiloxane copolymers in which both ends of the molecular chain are closed by dimethylvinylsiloxy groups; and dimethylsiloxanelmethylvinylsiloxane/methylphenylsiloxane copolymers in which both ends of the molecular chain are closed by dimethylvinylsiloxy groups.

Component (D) may also be an organopolysiloxane copolymer consisting of siloxane units of the formula $R_3SiO_{1/2}$, siloxane units of the formula $R_2R^1SiO_{1/2}$, and siloxane units of the formula $SiO_{4/2}$; organopolysiloxane copolymers consisting of siloxane units of the formula $R_2R^1SiO_{1/2}$, and siloxane units of the formula $SiO_{4/2}$; organopolysiloxane copolymers consisting of siloxane units of the formula $RR^1SiO_{2/2}$, and siloxane units of the formula $RSiO_{3/2}$ or $R^1SiO_{3/2}$; and mixtures of two or more of such organopolysiloxanes. In these formulae, R is a monovalent hydrocarbon group other than alkenyl. Examples of appropriate R groups are mentioned above. $R^1$ is an alkenyl group such as vinyl, allyl, butenyl, pentenyl, hexenyl, and heptenyl.

The content of component (D) in the crosslinkable composition should be such as to provide a weight ratio of component (A) to component (B) in the range of 0.1:99.9 to 99.9:0.1. A ratio in the range of 0.5:99.5 to 50:50 is especially preferred. If the content of component (D) exceeds the upper limit of the range, the affinity of the crosslinked particles for the organic oil tends to drop. If the content of component (D) is less than the lower limit of the range, the affinity of the crosslinked particles for the silicone oil tends to drop.

The crosslinkable composition may contain other types of optional components in addition to component (D), including reaction inhibiting agents used to adjust the hydrosilylation reaction; reinforcing fillers such as precipitated silica, fumed silica, calcined silica, and fumed titanium oxide; nonreinforcing fillers such as pulverized quartz, diatomaceous earth, aluminosilicates, iron oxide, zinc oxide, and calcium carbonate; and fillers obtained by subjecting such fillers to a surface treatment using organosilicon compounds typified by hexamethylsilane, trimethylchlorosilane, polydimethylsiloxanes, or polymethylhydridosiloxanes.

Preferably, the liquid crosslinkable composition should be one that will produce an elastomer, rubber, gel, or resinous crosslinked product as a result of crosslinking by means of the hydrosilylation reaction.

In the emulsion, the mean particle size of crosslinked particles should be 0.05 to 100 µm, preferably 0.1 to 100 µm, more preferably 0.1 to 50 µm. When the mean particle size of the liquid droplets of the silicone oil or organic oil is 0.2 to 500 µm, then the mean particle size of the crosslinked particles should be 0.1 to 100 µm, and a mean particle size of 0.1 to 50 µm is especially desirable. When the mean particle size of the liquid droplets of the silicone oil or organic oil is 0.5 to 500 µm, then the mean particle size of the crosslinked particles should be 0.1 to 100 µm, and a mean particle size of 0.1 to 50 µm is especially desirable. When the mean particle size of the liquid droplets of the silicone oil or organic oil is 0.5 to 200 µm, then the mean particle size of the crosslinked particles should be 0.1 to 100 µm, and a mean particle size of 0.1 to 50 µm is especially desirable.

It is difficult to prepare crosslinked particles whose mean particle size is smaller than the lower limit of the above range. Crosslinked particles whose mean particle size exceeds the upper limit of the above range tend to lower the stability of the emulsion. In any case, it should be understood that the particle size of the crosslinked particles in the emulsion is smaller than the droplet size of the silicone oil or the organic oil. The shape of the crosslinked particles may be spherical, spindle shaped, flat, or amorphous in nature. A spherical shape is preferred.

There are no particular restrictions on the silicone oil or organic oil used in the emulsion provided that the oil is present in a sufficient quantity so that the crosslinked particles can be contained in droplets of the oil. Therefore, the content of the silicone oil or organic oil should be 50 to 5,000 parts by weight per 100 parts by weight of the liquid crosslinkable composition forming the crosslinked particles. The content is preferably 100 to 5,000 parts by weight, more preferably 200 to 5,000 parts by weight, and most preferably 250 to 2,000 parts by weight.

There are no restrictions on the water content of the emulsion, however, it is desirable that the water content be 5 to 99 weight percent of the emulsion as a whole. A water content of 10 to 80 weight percent is especially desirable.

A surfactant can be used to disperse droplets of the silicone oil or organic oil containing the crosslinked particles in water in the emulsion with good stability. Some examples of cationic surfactants that can be used are alkyltrimethyl ammonium salts, dialkyldimethyl ammonium salts, tetraalkyl ammonium salts, trialkylbenzyl ammonium salts, alkylpyridinium salts, or polyethylene polyamine fatty acid amide salts.

Some examples of anionic surfactants that can be used are fatty acid salts, alkylbenzene sulfonates, alkylnaphthalene sulfonates, alkyl sulfonates, α-olefin sulfonates, dialkyl sulfosuccinates, α-sulfonated fatty acid salts, alkylsulfates, sulfated oils and fats, polyoxyethylene alkyl ether sulfates, polyoxyethylene alkylphenyl ether sulfates, polyoxyethylene styrenated phenyl ether sulfates, alkyl phosphates, polyoxyethylene alkyl ether phosphates, or polyoxyethylene alkylphenyl ether phosphates.

Some examples of amphoteric surfactants that can be used are N,N-dimethyl-N-alkyl-N-carboxymethyl ammonium betaines, N,N-dialkylaminoalkylene carboxylates, N,N,N-trialkyl-N-sulfoalkylene ammonium betaines, or N,N-dialkyl-N,N-bispolyoxyethylene ammonium sulfuric acid ester betaines.

Some examples of nonionic surfactants that can be used are polyoxyethylene alkyl ethers, polyoxyethylene alkenyl ethers, polyoxyethylene alkylphenyl ethers, polyoxyethylene polystyryl phenyl ethers, polyoxyethylene/polyoxypropylene glycols, polyoxyethylene/polyoxypropylene alkyl ethers, fatty acid partial esters of polyhydric alcohols such as sorbitan fatty acid esters, glycerol fatty acid esters, decaglycerol fatty acid esters, polyglycerol fatty acid esters, propylene glycol pentaerythritol fatty acid esters or propylene glycol pentaerythritol fatty acid esters, fatty acid partial esters of polyoxyethylene and polyhydric alcohols such as polyoxyethylene sorbitan fatty acid esters or polyoxyethylene glycerol fatty acid esters, polyoxyethylene fatty acid esters, polyglycerol fatty acid esters, polyoxyethylenated castor oil, fatty acid diethanolamides, polyoxyethylene alkylamines, triethanolamine fatty acid partial esters, and trialkylamine oxides.

Nonionic surfactants are preferred. There are no restrictions on the content of the surfactant in the emulsion, but it should be present at 0.1 to 20 parts by weight per 100 parts by weight of the silicone oil or organic oil containing the crosslinked particles. A surfactant content in the range of 0.5 to 10 parts by weight is especially desirable.

In order to prepare the emulsion, the liquid crosslinkable composition containing the non-crosslinkable silicone or organic oil is dispersed in water, and crosslinking is carried out by means of a hydrosilylation reaction. The non-crosslinkable silicone or organic oil does not participate in the hydrosilylation reaction of the liquid crosslinkable composition. Examples of such oils include the silicone and organic oils described above.

The liquid crosslinkable composition consists of components (A)–(C), the optional component (D), and other optional components. The liquid crosslinkable composition containing the hydrosilylation catalyst can be prepared in water by dispersing the liquid crosslinkable composition to which component (C) has been added beforehand in water, or by dispersing the liquid crosslinkable composition without component (C) in water, and then adding component (C) to the water. In the latter case, component (C) can be added as an aqueous dispersion in which it has been dispersed as a mean particle size of 1 µm or less.

The content of the non-crosslinkable silicone oil or the non-crosslinkable organic oil in the liquid crosslinkable composition should be an amount exceeding the amount of non-crosslinkable silicone or organic oil that can be contained in the crosslinked product of the liquid crosslinkable composition. This amount can vary according to the combination of liquid crosslinkable composition and non-crosslinkable silicone or organic oil that is used, but generally the amount of non-crosslinkable silicone oil or organic oil that is used should be 50 to 5,000 parts by weight per 100 parts by weight of liquid crosslinkable composition. A content of 100 to 5,000 parts by weight is desirable, a content of 200 to 5,000 parts by weight is more desirable, and a content of 250 to 2,000 parts by weight is especially desirable.

Methods used to disperse the liquid crosslinkable composition in water include the use of apparatus such as a homomixer, paddle mixer, Henschel mixer, homodisperser, colloid mixer, propeller agitator, homogenizer, in-line continuous emulsifier, ultrasonic emulsifier, or vacuum kneader.

There are no restrictions on the amount of water that can be added, however, it is desirable that the amount of water added be 5 to 99 weight percent of the overall amount of the emulsion, and a water content in the range of 10 to 80 weight percent is desirable.

To achieve a stable dispersion of the liquid crosslinkable composition in water, it is desirable to include a cationic surfactant, anionic surfactant, amphoteric surfactant, or nonionic surfactant, of the types described above, and a nonionic surfactant is desirable. There are no restrictions on the amount of surfactant that can be added, however, it should be an amount in the range of 0.1 to 20 parts by weight per 100 parts by weight of the liquid crosslinkable composition containing the non-crosslinkable silicone or organic oil, and an amount in the range of 0.5 to 10 parts by weight is especially desirable.

The emulsion of the liquid crosslinkable composition that is obtained can be crosslinked by subjecting the liquid crosslinkable composition dispersed in water to a hydrosilylation reaction, either by heating the dispersion of the composition or allowing the dispersion to stand at room temperature.

An oil composition in which crosslinked particles are dispersed in the silicone or organic oil can be obtained by removing water from the emulsion, and it can be used as a cosmetic raw material. Some examples of methods that can be used to remove water from the emulsion include air draft drying, hot air draft drying, vacuum drying, and drying by heating. In this type of cosmetic raw material, the crosslinked particles are contained in the silicone or organic oil and have good dispersibility. The form of this cosmetic raw material can be liquid, crème, paste, grease, powder, or bulk. Such a cosmetic raw material consisting of the silicone or organic oil composition is also useful as a non-water based cosmetic raw material.

The cosmetic raw material may separately contain other types of organic oils such as liquid paraffin, isoparaffin, hexyl laurate, isopropyl myristate, myristyl myristate, cetyl myristate, 2-octyldecyl myristate, isopropyl palmitate, 2-ethylhexyl palmitate, butyl stearate, decyl oleate, 2-octyldecyl oleate, myristyl lactate, cetyl lactate, lanolin acetate, stearyl alcohol, cetostearyl alcohol, oleyl alcohol, avocado oil, almond oil, olive oil, cacao oil, jojoba oil, sesame oil, safflower oil, soybean oil, camellia oil, squalane, persic oil, castor oil, mink oil, cottonseed oil, coconut oil, egg yolk oil, and lard; glycol ester oils such as polypropylene glycol monooleate and neopentyl glycol 2-ethylhexanoate; polyhydric alcohol ester oils such as isostearic acid triglyceride and coconut oil fatty acid triglyceride; polyoxyalkylene ether oils such as polyoxyethylene lauryl ether and polyoxypropylene cetyl ether; and other types of silicone oils.

The cosmetic of the invention consists of the cosmetic raw material which is the emulsion of the silicone or organic oil containing the crosslinked particles, and other cosmetic raw materials. The cosmetic can be any of various types among which are cleansing cosmetics such as soaps, body shampoos, and face cleansing cremes; basic cosmetics such as toilet waters, cremes, emulsions, and packs; makeup cosmetics such as powders and foundations, lipsticks, rouges, eye cosmetics such as eye shadow, eye liners and mascara, and manicure cosmetics; hair cosmetics such as shampoos, hair rinses, hair conditioners, hair treatments, setting lotions, gel styling agents, hair liquids, hair tonics, hair crèmes, hair-growing agents, hair nutrient agents, hair dyes, and hair dressings; aromatic cosmetics such as perfumes and eau de cologne; toothpaste; bath agents; and special cosmetics such shaving lotions, antiperspirants, deodorants, and sun screens.

Especially desirable are the basic cosmetics, skin cosmetics such as makeup cosmetics, and hair cosmetics. The cosmetic formulations can be in the form of water based liquid formulations, oil based liquid formulations, emulsion formulations, crème formulations, semisolid formulations, solid formulations, and powdered formulations. The cosmetic can be used in spray form.

The other cosmetic raw material used in the cosmetic can be of various types among which are oils and fats such as avocado oil, almond oil, olive oil, cacao oil, sesame oil, wheat germ oil, safflower oil, jojoba oil, shea butter, turtle oil, camellia oil, persic oil, castor oil, grape oil, macadamia oil, mink oil, egg yolk oil, Japan wax, coconut oil, rose hip oil, and hardened oils; waxes such as orange roughy oil, carnauba wax, candelilla wax, spermaceti wax, montan wax, beeswax, and lanolin; hydrocarbons such as liquid paraffin, vaseline, paraffin, ceresin, microcrystalline wax, and squalane; higher fatty acids such as lauric acid, myristic acid, palmitic acid, stearic acid, oleic acid, behenic acid, udecylenic acid, oxystearic acid, linolic acid, lanolic acid, and synthetic fatty acids; alcohols such as ethyl alcohol, isopropyl alcohol, lauryl alcohol, cetyl alcohol, cetostearyl alcohol, stearyl alcohol, oleyl alcohol, behenyl alcohol, lanolin alcohol, hydrogenated lanolin alcohol, hexyldecanol, octyldecanol, and isostearyl alcohol; sterols such as cholesterol, dihydrochloresterol, and phytosterol; fatty acid esters such as ethyl linolate, isopropyl myristate, isopropyl lanolin fatty acid esters, hexyl laurate, myristyl myristate, cetyl myristate, octyldecyl myristate, decyl oleate, octyldecyl oleate, hexyldecyl dimethyloctanoate, cetyl isooctanoate, cetyl palmitate, glycerol trimyristate, glycerol tri(caprylcaproate), propylene glycol dioleate, glycerol triisostearate, glycerol tri(isooctanoate), cetyl lactate, myristyl lactate, and diisostearyl malate; and moisturizers such as glycerol, propylene glycol, 1,3-butylene glycol, polyethylene glycol, sodium 1-pyrrolidone carboxylate, sodium lactate, sorbitol, and sodium hyaluronate.

Some other types of cosmetic raw materials which can be used in the cosmetic are anionic surfactants such as higher fatty acid soaps, higher alcohol sulfuric acid esters, N-acyl glutamates, and phosphoric acid esters; cationic surfactants; amphoteric surfactants such as betaine, amino acid, imidazoline, and lecithin type surfactants; nonionic surfactants such as polyhydric alcohol ester and ethylene oxide condensed type surfactants; colored pigments such as iron oxide; white pigments such as zinc oxide, titanium oxide, and zirconium oxide; body pigments such as mica, talc and ceresite; silicone oils such as dimethylpolysiloxanes, methylphenylpolysiloxanes, octamethylcyclotetrasiloxane, decamethylcyclopentasiloxane, polyether modified silicone oils, and amino modified silicone oils; purified water; viscosity enhancers such as carrageenan, alginic acid, gum arabic, tragacanth gum, pectin, starch, xanthan gum, polyvinyl alcohols, polyvinylpyrrolidones, sodium polyacrylates, and polyethylene glycols; coating or film forming agents such as silicone/acrylic copolymers, silicone resins, and acrylic polymers; ultraviolet absorbing agents; antifungal agents; antiinflammatory agents; antiperspirants; preservatives; fragrances; oxidation inhibitors; pH adjusting agents; and spray agents.

When the cosmetic is a hair cosmetic, the other hair cosmetic raw materials which can be used are oils and fats, surfactants, coating or film forming agents, antidandruff agents, oxidation inhibitors, and wetting agents. Some examples of oils and fats include waxes such as microcrystalline wax, paraffin wax, spermaceti wax, beeswax, Japan wax, cane sugar wax, and mixtures of such waxes; hydrocarbon oils such as liquid paraffin, α-olefin oligomers, squalane, and mixtures of such hydrocarbon oils; linear or branched, saturated or unsaturated, hydroxy substituted or unsubstituted alcohols such cetanol, stearyl alcohol, isostearyl alcohol, alcohols derived from hardened castor oil, behenyl alcohol, lanolin alcohol, or mixtures of such alcohols; linear or branched, saturated or unsaturated, hydroxy substituted or unsubstituted higher fatty acids such as palmitic acid, myristic acid, oleic acid, stearic acid, hydroxystearic acid, isostearic acid, behenic acid, castor oil fatty acids, coconut fatty acids, or mixtures of such fatty acids; oily esters such as olive oil, coconut oil, rapeseed oil, palm oil, palm kernel oil, castor oil, hardened castor oil, peanut oil, beef tallow, hydrogenated beef tallow, jojoba oil, hardened jojoba oil, monostearic acid glyceride, monooleic acid glyceride, dipalmitic acid glyceride, trimyristic acid glyceride, oleyl oleate, isostearyl isostearate, palmityl behenate, isopropyl palmitate, stearyl acetate, and dihydroxystearic acid ester.

Some other types of hair cosmetic raw materials which can be used are linear, branched, or cyclic low molecular weight silicone oils; silicone oils such as amino modified silicone oils, fatty acid modified silicone oils, alcohol modified silicone oils, polyether modified silicone oils, silicone oils containing phosphoric acid or phosphate groups, silicone oils containing sulfuric acid or sulfate groups, silicone oils containing fluorine modified alkyl groups, alkyl modified silicone oils, and epoxy modified silicone oils; coating or film forming agents such as high-molecular weight silicone oils which are soluble in solvents and are in liquid or raw rubber state at room temperature, silicone oils which possess thermoplasticity, silicone/acrylic copolymers, silicone resins, acrylic polymers, or mixtures of such coating or film forming agents.

Examples of anionic surfactants include glycerol fatty acid esters such as glycerol monostearate, sorbitan fatty acid esters such as sorbitan monopalmitate, polyoxyethylene alkyl ethers such as polyoxyethylene cetyl ethers, polyoxyethylene fatty acid esters such as polyoxyethylene stearic acid esters, and polyoxyethylene sorbitan monolaurate; nonionic surfactants such as polyoxyethylene alkylphenyl ethers, polyoxyethylene castor oil, polyoxyethylene hardened castor oil, and fatty acid alkylol amides; cationic surfactants including monoalkyl trimethyl ammonium salts such as stearyl trimethyl ammonium chloride, behenyl trimethyl ammonium chloride, dialkyl dimethyl ammonium salts such as distearyl dimethyl ammonium chloride and dibehenyl dimethyl ammonium chloride; and amphoteric surfactants.

Some examples of coating or film forming agents include polymers of (meth)acrylic type radical polymerizable monomers and copolymers of silicone compounds, poly-N-acylalkylene imines, poly-N-methyl pyrrolidones, silicone resins modified by fluoro-group containing organic groups or amino groups, and unmodified silicone resins. Some examples of antidandruff agents include sulfur, selenium sulfide, zinc pyrithione, OCTOPYROX®, i.e., piroctone olamine, zinc pyridinium-1-thiole-N-oxide, salicylic acid, 2,4,4'-trichloro-2'-hydroxydiphenyl ether, and 1-hydroxy-2-pyridine thione. Some examples of oxidation inhibitors include butylated hydroxyanisole (BHA), butylated hydroxytoluene (BHT), and γ-oryzanol. Some examples of wetting agents include hexylene glycol, polyethylene glycols, sodium pyroglutamate, propylene glycol, sorbitol, and glycerol.

Some other optional components for hair cosmetics are tactile sensation improving agents such as squalene, lanolin, perfluoropolyethers, and cationic polymers; antifreeze agents such as ethanol, isopropyl alcohol, 1,3-butylene glycol, ethylene glycol, propylene glycol and glycerol; chelating agents such as ethylene diamine tetraacetic acid, citric acid, ethane-1-hydroxy-1,1-diphosphonic acid, and salts of such acids; ultraviolet absorbing agents among which are benzophenone derivatives such as 2-hydroxy-4-methoxybenzophenone, benzotriazole derivatives such as 2-(2'-hydroxy-5'-methylphenyl)benzotriazole, and cinnamic acid esters; fungicidal agents such as triclosan and trichlorocarbane; anti-inflammatory agents such as potassium glycyrrhizinate and tocopherol acetate; preservatives such as methylparaben and butylparaben; coloring agents such as pearlizing agents, pigments, and dyes; spray agents; vitamins; hair nutrients; hormones; and fragrances.

When the hair cosmetic is water based, it may also contain in addition to water, water soluble macromolecular compounds such as xanthan gum, guar gum, carboxymethylcellulose, polyvinyl alcohols, polyvinylpyrrolidones, carboxyvinyl polymers, hydroxyethylcellulose, and polyoxyethylene glycol distearates, for stabilizing the hair cosmetic. Such water soluble macromolecular compounds or ethanol can also be added as viscosity adjusting agents in the hair cosmetic.

In cosmetics prepared according to this invention, it is desirable that the content of cosmetic raw material, which is the emulsion of silicone or organic oil containing the crosslinked particles, be in the range of 0.1 to 99.9 weight percent of the cosmetic, calculated as the solids content of components other than water. A content in the range of 0.5 to 99 weight percent is especially desirable. If the content exceeds the upper limit of the range, the effect of the cosmetic tends to be lost. If the content is less than the lower limit of the range, it tends to become difficult to improve the feel of use of the cosmetic by adding the cosmetic raw material.

When the cosmetic is one in which the cosmetic raw material is the oil composition and other cosmetic raw materials, the other cosmetic raw materials can be of the same character as those noted above. In such a cosmetic, the content of the oil composition should be in the range of 0.5 to 99.0 weight percent of the cosmetic, and a content in the range of 1.0 to 95 weight percent is desirable. If its content exceeds the upper limit of the range, the effect of the cosmetic tends to be lost. If the content is less than the lower limit of the range, it tends to become difficult to improve the feel of use of the cosmetic by adding the oil composition.

The method of manufacturing cosmetics according to this invention comprises simply mixing the cosmetic raw material, i.e., the emulsion of silicone or organic oil containing the crosslinked particles, with the other cosmetic raw materials. The types of other cosmetic raw materials used in the method include the same other cosmetic raw materials as described above. According to the method, the emulsion of the silicone or organic oil containing the crosslinked particles can be uniformly dispersed in the cosmetic without using special apparatus or applying high shear. The cosmetic can be manufactured using either a batch or continuous system. Some examples of apparatus that can be used include homomixers, paddle mixers, Henschel mixers, homodispersers, colloid mills, propeller agitators, homogenizers, in-line continuous emulsifiers, ultrasonic emulsifiers, and vacuum kneaders.

When the cosmetic is one in which water is removed from the emulsion of silicone or organic oil containing the crosslinked particles during its manufacture, water can be removed by pressure reduction, heating, air draft drying, or bringing the composition in contact with a moisture absorbing agent.

In preparing cosmetics, the amount of cosmetic raw material consisting of the emulsion of silicone or organic oil containing the crosslinked particles, should be added in a range of 0.1 to 99.9 weight percent of the cosmetic, calculated as the content of solid components other than water. An amount in the range of 0.5 to 99 weight percent is desirable. If the amount exceeds the upper limit of the range, the effect of the cosmetic tends to be lost. If the amount is less than the lower limit of the range, it tends to become difficult to improve the feel of use of the cosmetic by adding the emulsion.

WORKING EXAMPLES

The cosmetic raw material, cosmetics, and the cosmetic manufacturing method, will be described in more detail in the following working examples. Viscosity values in these working examples are values determined at 25° C. The mean particle size and stability of the emulsion, the mean particle size and the dispersibility of the crosslinked particles, and the characteristics of the oil composition, were each determined by separate protocols described below.

Mean Particle Size of the Emulsion

The emulsion was measured using a laser diffraction type particle size distribution measuring device, Model LA-500 manufactured by Horiba Seisakusho. A median size was obtained which was a particle size corresponding to 50 percent of the cumulative distribution, and this median value was used as the mean particle size.

Stability of the Emulsion 180 ml of the emulsion was tightly sealed in a 225 ml glass bottle having a depth of 105 mm and a diameter of 50 mm. It was allowed to stand in the bottle for one week at room temperature. After a week, the thickness of the aqueous layer that separated from the emulsion was measured.

Mean Particle Size of Crosslinked Particles

The emulsion was dried by means of an air draft on a glass plate, and a sample was prepared by collecting the crosslinked particles under a stereoscopic microscope. The sample was observed by means of an electron microscope, and the mean particle size was determined from 10 particle size measurements.

Dispersibility of Crosslinked Particles

The emulsion was dried using an air draft on a glass plate. The shape, conditions of aggregation, and the distribution of the crosslinked particles, were observed under a stereoscopic microscope. Samples in which all of the crosslinked particles were dispersed as primary particles were graded as "O", samples showing aggregate particles with sizes of several hundred $\mu$m or primary particles exceeding 500 $\mu$m in size were graded as "x", and samples intermediate between these two states were graded as "$\Delta$".

Viscoelasticity of Oil Composition

The storage elastic modulus $G'(\times 10^3$ dyne/cm$^2$), the loss elastic modulus $G''(\times 10^3$ dyne/cm$^2$), and the loss tangent tan $\delta$, of each oil composition were measured by means of an ARES viscoelasticity measuring apparatus manufactured by Reometric Scientific Company. The measurements were carried out at room temperature using 25 mm parallel plates, a gap of 0.5 to 0.6 mm, a strain of 10 percent, and a vibrational frequency of 0.1 to 50 rad/s.

Preparation of Cosmetic Raw Materials

Cosmetic raw materials were prepared according to the following examples.

Reference Example 1

17.0 parts by weight of a polypropylene oxide with an average molecular weight of 3,000, a viscosity of 390 mPa.s and containing allyl groups on both ends of the molecular chain, 3.0 parts by weight of an organopolysiloxane of the formula $(CH_3SiO_{3/2})_{0.1}[(CH_3)HSiO_{2/2}]_{1.5}[(CH_3)_2SiO_{2/2}]_{1.5}[(CH_3)_3SiO_{1/2}]_{0.5}$, having a viscosity of 20 mPa.s and which had at least three hydrogen atoms bonded to silicon atoms in each molecule, and 80 parts by weight of a dimethylpolysiloxane with a viscosity of 100 mPa.s in which both ends of the molecular chain were closed by trimethylsiloxy groups, were mixed to provide a liquid crosslinkable composition. Then 53 parts by weight of a 3 weight percent aqueous solution of a polyoxyethylene nonylphenyl ether with an HLB of 13.1 was added to the liquid crosslinkable composition, 50 parts by weight of pure water was added, to provide an aqueous emulsion of the liquid crosslinkable composition.

A separate aqueous emulsion was prepared of platinum catalyst having a mean particle size of platinum of 0.05 $\mu$m and a platinum metal concentration of 0.05 weight percent. Its major ingredient was a 1,3-divinyl-1,1,3,3-tetramethyldisiloxane complex of platinum. This emulsion was mixed with the aqueous emulsion of liquid crosslinkable composition, such that the concentration of platinum metal with respect to the solid content of the emulsion was 20 ppm. The mixed emulsion was used as the aqueous emulsion of liquid crosslinkable composition.

Crosslinking was carried out via hydrosilylation reaction effected by allowing the emulsion to stand for one day at room temperature. This provided a silicone oil emulsion in which crosslinked particles were contained in silicone oil droplets which were in turn dispersed in water. The emulsion was designated as cosmetic raw material (A).

The emulsion was transferred to an aluminum dish with a diameter of 5 cm, and it was air dried for three days in an air draft. This caused the water to be removed, producing a silicone oil composition consisting of the silicone oil and the crosslinked particles. The silicone oil composition was in crème form. When this silicone oil composition was observed under a stereoscopic microscope, it was found that the crosslinked particles were uniformly dispersed in the silicone oil, and the shape of the crosslinked particles was spherical.

Reference Example 2

A liquid crosslinkable composition was prepared by mixing together at 5° C., 2.46 parts by weight of 1,5-hexadiene of molecular weight 82.15, 17.54 parts by weight of a dimethylsiloxane/methylhydridosiloxane copolymer with a viscosity of 50 mPa.s having both ends of the molecular chain closed by trimethylsiloxy groups and containing at least three hydrogen atoms bonded to silicon atoms in each molecule, 80 parts by weight of a dimethylpolysiloxane with a viscosity of 6 mPa.s having both ends of the molecular chain closed by trimethylsiloxy groups, and an isopropyl alcohol solution of chloroplatinic acid in an amount such that the platinum metal concentration in the composition was 50 ppm in weight units.

The liquid crosslinkable composition was quickly mixed with 100 parts by weight of a 1.65 weight percent aqueous solution of polyoxyethylene (9) nonylphenyl ether adjusted to a temperature of 25° C., and the mixture was emulsified using a colloid mill. The emulsion was added to 200 parts by weight of pure water, producing an aqueous emulsion of liquid crosslinkable composition. Crosslinking was accomplished by hydrosilylation, effected by allowing the emulsion to stand quietly for 24 hours at 35° C., producing a silicone oil emulsion in which crosslinked particles were contained in silicone oil droplets, and the droplets of silicone oil containing the crosslinked particles were in turn dispersed in water. This emulsion was designated at cosmetic raw material (B).

Emulsion (B) was transferred to an aluminum dish with a diameter of 5 cm, and it was air dried for 3 days in an air draft. This removed water from Emulsion (B), producing a silicone oil composition consisting of the silicone oil and crosslinked particles. The silicone oil composition was in a crème-form. When observed under a stereoscopic microscope, it was found that the crosslinked particles were uniformly dispersed in the silicone oil, and the shape of the crosslinked particles was spherical.

Reference Example 3

Composition (I) was prepared by uniformly mixing 100 parts by weight of a dimethylpolysiloxane with a viscosity of 1,000 mPa.s having both ends of the molecular chain closed by hydroxy groups and with a hydroxy group content of 1.3 weight percent, 10 parts by weight of a methylhydridopolysiloxane with a viscosity of 10 mPa.s having both ends of the molecular chain closed by trimethylsiloxy groups and a content of hydrogen atoms bonded to silicon atoms of 1.5 weight percent, and 50 parts by weight of a dimethylpolysiloxane with a viscosity of 1,000 mPa.s having both ends of the molecular chain closed by trimethylsiloxy groups.

Composition (I) was prepared by uniformly mixing 100 parts by weight of a dimethylpolysiloxane with a viscosity of 1,000 mPa.s having both ends of the molecular chain closed by hydroxy groups with a hydroxy group content of 1.3 weight percent, 50 parts by weight of a dimethylpolysiloxane with a viscosity of 1,000 mPa.s having both ends of the molecular chain closed by trimethylsiloxy groups, and 1.5 parts by weight of dibutyltin octoate.

A liquid crosslinkable composition was prepared by uniformly mixing composition (I) and composition (II) at a weight ratio of 1:1. The mixture was emulsified by adding 5 weight percent Tergitol® TMN-6 nonionic surfactant, an ethylene oxide adduct of trimethylnonanol of Union Carbide Company, and 1,700 parts by weight of ion exchanged water, producing an emulsion of the liquid crosslinkable composition. Water was removed from the emulsion by spraying the emulsion with a spray drier having an inlet temperature of 300° C. and an outlet temperature of 100° C., and crosslinked silicone particles were obtained at a yield of 98 percent. These crosslinked silicone particles were designated as cosmetic raw material (C). The crosslinked silicone particles were rubber particles of spherical shape. No bleeding of silicone oil from the crosslinked silicone particles was observed.

Reference Example 4

A liquid crosslinkable composition was produced by mixing 44.5 parts by weight of a dimethylpolysiloxane with a viscosity of 5 mPa.s having both ends of the molecular chain closed by vinylmethylsiloxy groups, 100 parts by weight of a methylhydridopolysiloxane with a viscosity of 20 mPa.s having both ends of the molecular chain closed by trimethylsiloxy groups and a content of hydrogen atoms bonded to silicon atoms of 1.5 percent, and 758 parts by weight of a dimethylpolysiloxane with a viscosity of 6 mPa.s having both ends of the molecular chain closed by trimethylsiloxy groups; and then adding 0.5 parts by weight of a 2 weight percent isopropyl alcohol solution of chloroplatinic acid. The composition was agitated for 2 hours while being heated to a temperature of 70–80° C., and the liquid crosslinkable composition was crosslinked by a hydrosilylation reaction to produce a soft silicone composition. When the soft silicone composition was kneaded under a shearing force by means of a three roll mill, a paste form of silicone composition was produced. The paste was designated as cosmetic raw material (D). When silicone composition (D) was observed under a stereoscopic microscope, it was found that amorphous crosslinked silicone particles were dispersed in a silicone oil, but the dispersion was not uniform. In addition, the particle size of the crosslinked silicone particles was large, i.e., about 100–500 μm.

Reference Example 5

A liquid crosslinkable composition was prepared by uniformly mixing at 5° C., 2.46 parts of 1,5-hexadiene of molecular weight 82.15, 17.54 parts by weight of a dimethylsiloxane/methylhydridosiloxane copolymer with a viscosity of 50 mPa.s having at least three hydrogen atoms bonded to silicon atoms in each molecule and both ends of the molecular chain closed by trimethylsiloxy groups, 80 parts by weight of isoparaffin of viscosity of 2.4 mPa.s and carbon number of 16, sold under the name Isosol 400 by Nippon Sekiyu Kagaku K.K., and an isopropyl alcohol solution of chloroplatinic acid in an amount such that the platinum metal concentration in the composition was 50 ppm in weight units.

The liquid crosslinkable composition was quickly mixed with 100 parts by weight of a 1.65 weight percent aqueous solution of a polyoxyethylene (9) nonylphenyl ether adjusted to a temperature of 25° C., and the mixture was emulsified using a colloid mill. The emulsion was added to 200 parts by weight of pure water producing an aqueous emulsion of the liquid crosslinkable composition. Crosslinking was accomplished by a hydrosilylation reaction, effected by allowing the emulsion of the liquid crosslinkable composition to stand quietly for 24 hours at 35° C., producing an isoparaffin emulsion in which crosslinked particles were contained in isoparaffin droplets, and the droplets of isoparaffin containing the crosslinked particles were in turn dispersed in water. The emulsion was designated as cosmetic raw material (E).

Emulsion (E) was transferred to an aluminum dish with a diameter of 5 cm, and it was air dried for 3 days in an air draft. This removed water from the emulsion, producing an isoparaffin composition consisting of isoparaffin and crosslinked particles. The isoparaffin composition was in a crème form. When it was observed under a stereoscopic microscope, the crosslinked particles were observed to be uniformly dispersed in the isoparaffin, and the crosslinked particles were spherical.

Reference Example 6

A liquid crosslinkable composition was prepared by mixing 6.43 parts by weight of a polypropylene oxide of average molecular weight 3,000 and a viscosity of 390 mPa.s containing allyl groups on both ends of the molecular chain, 6.43 parts by weight of a dimethylpolysiloxane with a viscosity of 100 mPa.s having both ends of the molecular chain closed by dimethylvinylsiloxy groups, 7.14 parts by weight of an organopolysiloxane of the formula $(CH_3SiO_{3/2})_{0.1}[(CH_3)HSiO_{2/2}]_{1.5}[(CH_3)_2SiO_{2/2}]_{1.5}[(CH_3)_3SiO_{1/2}]_{0.5}$ having a viscosity of 20 mPa.s and at least three hydrogen atoms bonded to silicon atoms in each molecule, and 80 parts by weight of a dimethylpolysiloxane with a viscosity of 100 mPa.s having both ends of the molecular chain closed by trimethylsiloxy groups. 53 parts by weight of a 3 weight percent aqueous solution of a polyoxyethylene nonylphenyl ether with an HLB of 13.1 was added to the liquid crosslinkable composition, and then 50 parts by weight of pure water was added producing an aqueous emulsion of the liquid crosslinkable composition.

An aqueous emulsion of platinum type catalyst was separately prepared having a mean particle size of platinum catalyst of 0.05 µm, a platinum metal concentration of 0.05 weight percent, and consisting of a 1,3-divinyl-1,1,3,3-tetramethyldisiloxane solution, the main ingredient of which was a 1,3-divinyl-1,1,3,3-tetramethyldisiloxane complex of platinum. This emulsion was uniformly mixed with the aqueous emulsion of the liquid crosslinkable composition such that the concentration of platinum metal relative to the solid content of the emulsion was 20 ppm. This composition was used as the aqueous emulsion of liquid crosslinkable composition.

Crosslinking of the emulsion was carried out via a hydrosilylation reaction effected by allowing the emulsion to stand for 1 day at room temperature, producing a silicone oil emulsion in which crosslinked particles were contained in silicone oil droplets, and the silicone oil droplets containing the crosslinked particles were in turn dispersed in water. The emulsion was designated as cosmetic raw material (F).

Emulsion (F) was transferred to an aluminum dish with a diameter of 5 cm and air dried for 3 days in an air draft. This procedure removed water from the emulsion producing a silicone oil composition consisting of the silicone oil and crosslinked particles. The silicone oil composition was in crème form. When it was observed under a stereoscopic microscope, crosslinked particles were observed to be uniformly dispersed in the silicone oil, and the crosslinked particles were spherical.

Reference Example 7

A liquid crosslinkable composition was prepared by uniformly mixing at 5° C., 1.1 parts by weight of 1,5-hexadiene of molecular weight 82.15, 8.9 parts by weight of a dimethylpolysiloxane with a viscosity of 400 mPa.s having both ends of the molecular chain closed by dimethylvinylsiloxy groups, 10 parts by weight of a dimethylsiloxane/methylhydridosiloxane copolymer with a viscosity of 50 mPa.s having both ends of the molecular chain closed by trimethylsiloxy groups, 80 parts by weight of a dimethylpolysiloxane with a viscosity of 6 mPa.s having both ends of the molecular chain closed by trimethylsiloxy groups, and an isopropyl alcohol solution of chloroplatinic acid in an amount such that the platinum metal concentration in the composition was 50 ppm in weight units.

The liquid crosslinkable composition was quickly mixed with 100 parts by weight of a 1.65 weight percent aqueous solution of a polyoxyethylene (9) nonylphenyl ether adjusted to a temperature of 25° C. and emulsified using a colloid mill. The emulsion was added to 200 parts by weight of pure water producing an aqueous emulsion of liquid crosslinkable composition. Crosslinking was accomplished by hydrosilylation effected by allowing the emulsion to stand quietly for 24 hours at 35° C. producing a silicone oil emulsion in which crosslinked particles were contained in silicone oil droplets, and in which silicone oil droplets containing crosslinked particles were in turn dispersed in water. The emulsion was designated at cosmetic raw material (G).

Emulsion (G) was transferred to an aluminum dish with a diameter of 5 cm and air dried for 3 days in an air draft. This removed water for the emulsion producing a silicone oil composition consisting of the silicone oil and crosslinked particles. The silicone oil composition was in crème form. It was observed under a stereoscopic microscope and the crosslinked particles were observed to be uniformly dispersed in the silicone oil. The crosslinked particles were spherical.

Reference Example 8

A liquid crosslinkable composition was prepared by uniformly mixing at 5° C., 2.29 parts by weight of 1,5-hexadiene of molecular weight 82.15, 15.79 parts by weight of a dimethylsiloxane/methylhydridosiloxane copolymer with a viscosity of 50 mPa.s having both ends of the molecular chain closed by trimethylsiloxy groups and containing at least three hydrogen atoms bonded to silicon atoms in each molecule, 1.52 parts by weight of a dimethylpolysiloxane with a viscosity of 20,000,000 mPa.s having both ends of the molecular chain closed by trimethylsiloxy groups, 80 parts by weight of a dimethylpolysiloxane with a viscosity of 6 mPa.s having both ends of the molecular chain closed by trimethylsiloxy groups, and an isopropyl alcohol solution of chloroplatinic acid in an amount such that the platinum metal concentration in the composition was 50 ppm in weight units.

The liquid crosslinkable composition was quickly mixed with 100 parts by weight of a 1.65 weight percent aqueous solution of a polyoxyethylene (9) nonylphenyl ether adjusted to a temperature of 25° C. and emulsified using a colloid mill. The emulsion was added to 200 parts by weight of pure water producing an aqueous emulsion of liquid crosslinkable composition. Crosslinking was accomplished by means of a hydrosilylation reaction effected by allowing the emulsion to stand quietly for 24 hours at 35° C. This provided a silicone oil emulsion in which crosslinked particles were contained in silicone oil droplets, and in which the silicone oil droplets containing the crosslinked particles were in turn dispersed in water. The emulsion was designated as cosmetic raw material (H).

Emulsion (H) was transferred to an aluminum dish with a diameter of 5 cm and air dried for 3 days in an air draft. This removed water from the emulsion producing a silicone oil composition consisting of the silicone oil and crosslinked particles. The silicone oil composition was in crème form. When observed under a stereoscopic microscope, it was found that the crosslinked particles were uniformly dispersed in the silicone oil and were spherical.

Reference Example 9

360 parts by weight of a polydimethylsiloxane with a viscosity of 1,000,000 mPa.s having both ends of the molecular chain closed by trimethylsiloxy groups and 240 parts by weight of a polydimethylsiloxane with a viscosity of 20 mPa.s having both ends of the molecular chain closed by trimethylsiloxy groups, were uniformly mixed. 15 parts by weight of a polyoxyethylene lauryl ether with an HLB of 10.5, 35 parts by weight of a polyoxyethylene lauryl ether with an HLB of 16.7, and 40 parts by weight of water, were uniformly mixed with the polydimethylsiloxane mixture. The resulting mixture was emulsified. 310 parts by weight of water was added and the mixture was emulsified producing a silicone oil emulsion. This emulsion was designated as cosmetic raw material (I). The mean particle size of emulsion (I) was 0.5 µm.

TABLE 1

|  | Ref. Ex. 1 | Ref. Ex. 2 | Ref. Ex. 3 | Ref. Ex. 4 | Ref. Ex. 5 | Ref. Ex. 6 | Ref. Ex. 7 | Ref. Ex. 8 |
|---|---|---|---|---|---|---|---|---|
| Emulsion |  |  |  |  |  |  |  |  |
| Mean particle size (μm) | 5 | 4 | 5 | — | 5 | 4 | 5 | 4 |
| Stability (mm) | 0 | 0 | 49 | — | 2 | 2 | 2 | 0 |
| Cross-linked particles |  |  |  |  |  |  |  |  |
| Mean particle size (μm) | 3 | 2 | 5 | 17 | 3 | 2 | 3 | 2 |
| Dispersibility (mm) | ○ | ○ | X | — | ○ | ○ | ○ | ○ |
| Viscoelasticity of oil composition |  |  |  |  |  |  |  |  |
| G' 1/rad/s | 0.5 | 37 | — | 5.0 | 15 | 0.3 | 10 | 17 |
| 10 rad/s | 1.1 | 41 | — | 7.5 | 22 | 0.5 | 18 | 21 |
| G" 1/rad/s | 0.5 | 7.9 | — | 4.7 | 6.8 | 0.1 | 7.1 | 6.3 |
| 10 rad/s | 1.3 | 8.1 | — | 4.0 | 5.3 | 0.4 | 6.2 | 7.9 |
| Tan δ 1/rad/s | 1.2 | 0.22 | — | 0.82 | 0.46 | 0.57 | 0.71 | 0.37 |
| 10 rad/s | 1.2 | 0.22 | — | 0.58 | 0.25 | 0.82 | 0.34 | 0.38 |

Cosmetics and their Method of Manufacture

Cosmetics were prepared as described below and characteristics of the cosmetics were evaluated.

Tactile Sensation of Cosmetics on Fingers

Ten panelists were asked to use the cosmetic. When the number of panelists indicating that the tactile sensation of the cosmetic was good was 8 to 10 panelists, the cosmetic was graded as "O". When the number of panelists was 4 to 7 panelists, the cosmetic was graded as "Δ", and when the number of panelists was 3 or less, the cosmetic was graded as "x".

Feel of Cosmetic on Skin

Ten panelists were asked to use the cosmetic. When the number of panelists indicating that the feel of the cosmetic on their skin was good was 8 to 10 panelists, the cosmetic was graded as "O". When the number of panelists was 4 to 7 panelists, the cosmetic was graded as "Δ", and when the number of panelists was 3 or less, it was graded "x".

Conditions of Dispersion of Crosslinked Particles in Cosmetics

The cosmetic was applied as a thin coating to a glass plate and the particle size of the crosslinked particles in the cosmetic was observed under an optical microscope. The proportion of crosslinked particles with a particle size of 10 μm or less, the proportion of crosslinked particles with a particle size exceeding 10 μm, and the proportion of crosslinked particles with a particle size exceeding 50 μm, were determined. In this way, dispersibility of the crosslinked particles in the cosmetic was evaluated.

Working Example 1

An emulsion cosmetic was prepared by agitating for 3 minutes at 2500 rpm using a homodisperser, 52 parts by weight of cosmetic raw material (A) prepared in Reference Example 1, 5 parts by weight of octyl p-methoxycinnamate, 1 part by weight of α-monostearyl glyceryl ether polyoxyethylene sorbitan monooleic acid ester, 2 parts by weight of beeswax, 2 parts by weight of lanolin, 10 parts by weight of squalane, 10 parts by weight of liquid paraffin, 19 parts by weight of purified water, an appropriate amount of preservative and fragrance. The results of an evaluation of this cosmetic are shown in Table 2.

Working Example 2

An emulsion cosmetic was prepared by agitating for 3 minutes at 2500 rpm using a homodisperser, 52 parts by weight of cosmetic raw material (B) prepared in Reference Example 2, 5 parts by weight of octyl p-methoxycinnamate, 1 part by weight of α-monostearyl glyceryl ether polyoxyethylene sorbitan monooleic acid ester, 2 parts by weight of beeswax, 2 parts by weight of lanolin, 10 parts by weight of squalane, 10 parts by weight of liquid paraffin, 19 parts by weight of purified water, an appropriate amount of preservative and fragrance. The results of an evaluation of this cosmetic are shown in Table 2.

Comparative Example 1

An emulsion cosmetic was prepared by agitating for 3 minutes at 2500 rpm using a homodisperser, 3 parts by weight of the cosmetic raw material (C) prepared in Reference Example 3, 12 parts by weight of an emulsion with a concentration of 50 weight percent of a dimethylpolysiloxane having a viscosity of 100 mPa.s and both ends of the molecular chain closed by trimethylsiloxy groups, 5 parts by weight of octyl p-methoxycinnamate, 1 part by weight of α-monostearyl glyceryl ether polyoxyethylene sorbitan monooleic acid ester, 2 parts by weight of beeswax, 2 parts by weight of lanolin, 10 parts by weight of squalane, 10 parts by weight of liquid paraffin, 54 parts by weight of purified water, an appropriate amount of preservative and fragrance. The results of an evaluation of this cosmetic are shown in Table 2.

In Tables 2–8, WE refers to Working Example, and CE refers to Comparative Example.

TABLE 2

|  | WE 1 | WE 2 | CB 1 |
|---|---|---|---|
| Tactile sensation on fingers | o | o | Δ (roughness) |
| Feeling on skin | o | o | Δ (roughness) |
| Conditions of dispersion of crosslinked particles in cosmetic, Particle size |  |  |  |
| ≦10 μm, percent | 100 | 100 | 0 |
| 10 μ <, ≦50 μm, percent | 0 | 0 | 70 |
| 50 μm ≦, percent | 0 | 0 | 30 |

Working Example 3

A crème cosmetic was prepared by agitating for 5 minutes at 1500 rpm with a Henschel mixer, 40 parts by weight of the cosmetic raw material (E) prepared in Reference Example 5, 1 part by weight of silicone treated titanium oxide, 5 parts by weight of octyl p-methoxycinnamate, 10 parts by weight of a dimethylpolysiloxane having a viscosity of 20 mPa.s and both ends of the molecular chain closed by trimethylsiloxy groups, 3 parts by weight of polyoxyethylene (40) hardened castor oil, 30 parts by weight of squalane, 5 parts by weight of glycerol, 3 parts by weight of beeswax, an appropriate amount of preservative and fragrance, and an appropriate amount of purified water. The results of evaluating this cosmetic are shown in Table 3.

Working Example 4

A crème cosmetic was prepared by agitating for 5 minutes at 1500 rpm with a Henschel mixer, 40 parts by weight of the cosmetic raw material (F) prepared in Reference Example 6, 1 part by weight of silicone treated titanium oxide, 5 parts by weight of octyl p-methoxycinnamate, 10 parts by weight of a dimethylpolysiloxane having a viscosity of 20 mPa.s and both ends of the molecular chain closed by trimethylsiloxy groups, 3 parts by weight of polyoxyethylene (40) hardened castor oil, 30 parts by weight of squalane, 5 parts by weight of glycerol, 3 parts by weight of beeswax, an appropriate amount of a preservative and fragrance, and an appropriate amount of purified water. The results of evaluating this cosmetic are shown in Table 3.

Comparative Example 2

A crème cosmetic was prepared by agitating for 5 minutes at 1500 rpm with a Henschel mixer, 20 parts by weight of the cosmetic raw material (D) prepared in Reference Example 6, 1 part by weight of silicone treated titanium oxide, 5 parts by weight of octyl p-methoxycinnamate, 10 parts by weight of a dimethylpolysiloxane having a viscosity of 20 mPa.s and both ends of the molecular chains closed by trimethylsiloxy groups, 3 parts by weight of polyoxyethylene (40) hardened castor oil, 30 parts by weight of squalane, 5 parts by weight of glycerol, 3 parts by weight of beeswax, an appropriate amount of a preservative and a fragrance, and an appropriate amount of purified water. The results of evaluating this cosmetic are shown in Table 3.

TABLE 3

|  | WE 3 | WE 4 | CE 2 |
|---|---|---|---|
| Tactile sensation on fingers | o | o | o |
| Feeling on skin | o | o | Δ (roughness) |
| Conditions of dispersion of crosslinked particles in cosmetic, Particle size |  |  |  |
| ≦10 μm, percent | 100 | 100 | 0 |
| 10 μ <, ≦50 μm, percent | 0 | 0 | 60 |
| 50 μm ≦, percent | 0 | 0 | 40 |

Working Example 5

A water based cosmetic was prepared by agitating for 5 minutes at 1500 rpm using a Henschel mixer, 14 parts by weight of the cosmetic raw material (G) prepared in Reference Example 7, 2 parts by weight of 1,3-butylene glycol, 50 parts by weight of ethanol, 1 part by weight of a polyether modified silicone oil, 4 parts by weight of propylene glycol, 1 part by weight of polyoxyethylene (15) nonyl ether, 1 part by weight of silicone treated titanium oxide, a trace amount of a preservative and fragrance, and an appropriate amount of purified water. The results of evaluating this cosmetic are shown in Table 4.

Comparative Example 3

A water based cosmetic was prepared by agitating for 5 minutes at 1500 rpm with a Henschel mixer, one part by weight of the cosmetic raw material (C) prepared in Reference Example 3, 2 parts by weight of an emulsion having a concentration of 50 weight percent of a dimethylpolysiloxane with a viscosity of 100 mPa.s and both ends of the molecular chain closed by trimethylsiloxy groups, 4 parts by weight of purified water, 2 parts by weight of 1,3-butylene glycol, 50 parts by weight of ethanol, 1 part by weight of a polyether modified silicone oil, 4 parts by weight of propylene glycol, 1 part by weight of polyoxyethylene (15) nonyl ether, 1 part by weight of silicone treated titanium oxide, a trace amount of a preservative and fragrance, and an appropriate amount of purified water. The results of evaluating this cosmetic are shown in Table 4.

TABLE 4

|  | WE 5 | CE 3 |
|---|---|---|
| Tactile sensation on fingers | o | Δ (roughness) |
| Feeling on skin | o | Δ (roughness) |
| Conditions of dispersion of crosslinked particles in cosmetic, Particle size |  |  |
| ≦10 μm, percent | 100 | 0 |
| 10 μ <, ≦50 μm, percent | 0 | 70 |
| 50 μm ≦, percent | 0 | 30 |

Working Example 6

Cosmetic raw material (A) prepared in Reference Example 1 was spread on a metal dish to a thickness of 5 mm and air dried for one week at room temperature to provide a paste silicone composition in which crosslinked silicone particles were uniformly dispersed in silicone oil. The silicone composition was designated as cosmetic raw material (A'). The amount of heating weight loss shown by cosmetic raw material (A') when it was heated for 30 minutes at 105° C. was 0.2 weight percent.

10 parts by weight of cosmetic raw material (A'), 10 parts by weight of decamethylcyclopentasiloxane, 10 parts by weight of silicone treated titanium dioxide, and an appropriate amount of fragrance, were mixed using a Henschel mixer. 5 parts by weight of silicone treated flowers of zinc, 55 parts by weight of silicone treated talc, a silicone treated pigment, and an appropriate amount of fragrance, were added to produce a rouge. The characteristics of the rouge are shown in Table 5.

Comparative Example 4

A rouge was prepared as in Working Example 6 except that the cosmetic raw material (D) prepared in Working Example 4 was used instead of cosmetic raw material (A') used in Working Example 6. The characteristics of the rouge are shown in Table 5.

TABLE 5

|  | WE 6 | CE 4 |
|---|---|---|
| Tactile sensation on fingers | o | Δ (roughness) |
| Feeling on skin | o | Δ (roughness) |
| Conditions of dispersion of crosslinked particles in cosmetic, Particle size |  |  |
| ≦10 μm, percent | 100 | 0 |
| 10 μ <, ≦50 μm, percent | 0 | 70 |
| 50 μm ≦, percent | 0 | 30 |

Working Example 7

100 parts by weight of cosmetic raw material (B) prepared in Reference Example 2 and 10 parts by weight of a powdered silicone rubber having a mean particle size of 4 μm were mixed using a planetary mixer. Water was removed from the mixture under reduced pressure at 50° C. to provide a uniform paste silicone composition. The heating weight loss shown by the paste composition when it was heated for 30 minutes at 105° C. was less than 0.3 weight percent. 40 parts by weight of the paste composition, 10 parts by weight of ceresite pigment, 10 parts by weight of silicone treated titanium dioxide, 1.5 parts by weight of silicone treated red iron oxide, 4 parts by weight of silicone treated yellow iron oxide, 0.3 parts by weight of silicone treated black iron oxide, 4 parts by weight of wax, 1.3 parts by weight of carnauba wax, 33 parts by weight of squalane, 1 part by weight of sorbitan sesquioleate, 3 parts by weight of kaolin, and an appropriate amount of fragrance were mixed using a Henschel mixer. The result was a foundation with the characteristics shown in Table 6.

Comparative Example 5

A foundation was prepared in the same manner as Working Example 7 except that an equal amount of cosmetic raw material (D) prepared in Reference Example 4 was used, instead of the paste silicone composition used in Working Example 7. The powdered silicone rubber was also included in the foundation prepared in this example. The characteristics of the foundation are shown in Table 6.

TABLE 6

|  | WE 7 | CE 5 |
|---|---|---|
| Tactile sensation on fingers | o | Δ (roughness) |
| Feeling on skin | o | Δ (roughness) |
| Conditions of dispersion of crosslinked particles in cosmetic, Particle size |  |  |
| ≦10 μm, percent | 100 | 0 |
| 10 μ <, ≦50 μm, percent | 0 | 70 |
| 50 μm ≦, percent | 0 | 30 |

Working Examples 8 and 9 and Comparative Examples 6 and 7

Shampoos having a composition shown in Table 7 were prepared using cosmetic raw materials (B), (D), (H) and (I), prepared in Reference Examples 2, 4, 8, and 9, respectively. Hair was washed using the shampoos, and the rates of improvement in feel of hair following washing and combing were evaluated according to the procedures described below. The results of these evaluations are also shown in Table 7.

Evaluation of Improvement of Feel of Hair to Touch

A 10 gram hank of hair 20 cm in length was washed in a 2.5 weight percent aqueous solution of sodium polyoxyethylene lauryl ether sulfate and then rinsed with warm water and dried for 12 hours at 25° C. The pretreated hair was immersed in water for 30 seconds. Water was removed and the hair was washed for one minute with one gram of shampoo. The hair was rinsed twice for 20 seconds with warm water, water was removed, and the feel of the hair to touch was evaluated. The hair was then dried for 12 hours at 25° C. and the feel of the hair to touch was again evaluated.

Evaluation of Rate of Improvement in Combing Characteristics of the Hair

A 10 gram hank of hair 20 cm long was washed in a 2.5 weight percent aqueous solution of sodium polyoxyethylene lauryl ether sulfate, rinsed with warm water, and dried for 12 hours at 25° C. The hair was immersed in water for 30 seconds, wrapped in a towel, and water was removed by applying a pressure of 20 kgf/314 cm$^2$ for 5 seconds. The hair was brushed until there was no tangling. The pretreated hair was washed for one minute using one gram of shampoo, and then rinsed twice for 20 seconds with warm water. The hair was wrapped in a towel and water was removed by applying a pressure of 20 kgf/314 cm$^2$ for 5 seconds. The hair was brushed until thee was no tangling. The comb of an all purpose tensile tester made by Tester Sangyo K.K. was set on a moving stand, and one end of the hank of treated hair was fixed in place. The hank of hair was passed through the comb on the moving stand, and the maximum value of tensile force was measured when the stand moved at a speed of 200 mm per minute. This value was determined for hair hanks which had only been pretreated and for hair hanks which had been shampooed.

The rate of improvement in combing characteristics was determined by the formula Rate of improvement in combing characteristics in percent=100×(A−B)/A, where A is the tensile strength of hair subjected only to pretreatment, and B is the tensile strength of hair subjected to shampoo treatment.

Comparative Example 8

An attempt was made to prepare a shampoo in the same manner as in Working Example 8, except cosmetic raw material (C) prepared in Reference Example 3 was used instead of cosmetic raw material (B) prepared in Reference Example 2. However, it was found that the dispersibility of cosmetic raw material (C) was poor and aggregated particles with a diameter of 100 to 200 μm were created, with the result that it was not possible to prepare a uniform shampoo.

TABLE 7

| Cosmetic raw material | | | WE 8 B | WE 9 H | CE 6 D | CE 7 I |
|---|---|---|---|---|---|---|
| | Sodium POE (2) lauryl ether sulfate, parts by weight | | 12.0 | 12.0 | 12.0 | 12.0 |
| | Cosmetic raw materials, parts by weight | | 5.0 | 5.0 | 5.0 | 5.0 |
| | Water, parts by weight | | 83.0 | 83.0 | 83.0 | 83.0 |
| Rating | Improvement in feel of hair to touch | After removal of water | Smooth, no grating feel | Smooth, no grating feel | Somewhat smooth, but heavy | Smooth, but slight grating feel |
| | | After drying | Extremely smooth, good wet feel, no grating feel | Extremely smooth, good wet feel, no grating feel | Heavy | Smooth, but strong grating feel |
| | Rate of improvement in combing characteristics, % | | 34 | 39 | 7 | 25 |

Working Example 10 and Comparative Examples 9 and 10

Rinses were prepared by mixing cosmetic raw materials (B) and (C) at the rate of 2 weight percent with 98 weight percent of purified water. Using these rinses, the tactile sensation of hair on fingers and the quantity of crosslinked particles adhering to treated hair, were evaluated according to procedures described below. The results of these evaluations are shown in Table 8. As comparative examples, rinses were prepared using an increased amount of purified water instead of cosmetic raw material (B), and these comparative rinses were similarly evaluated. The results of evaluations of comparative rinses are also shown in Table 8.

Tactile Sensation of Hair on Fingers

A 10 gram hank of hair 20 cm long was washed in a 2.5 weight percent aqueous solution of sodium polyoxyethylene lauryl ether sulfate, rinsed with warm water, and dried for 12 hours at 25° C. The pretreated hank of hair was immersed in the respective rinses and then dried for 12 hours at 25° C. The slip properties and smoothness of treated hair were evaluated as □ which was used to indicate Very good, O as indicating Good, Δ indicating Neither Good nor Poor, and x used to indicate Poor.

Quantity of Crosslinked Particles Adhering to Hair

Rinsed hair was observed under an electron microscope and the number of crosslinked particles adhering to hair 100 μm long were counted from the side surface of the hair.

TABLE 8

| Cosmetic raw meterial | WE 10 B | CE 9 C | CE 10 None |
|---|---|---|---|
| Tactile sensation on fingers | | | |
| Slip | □ | Δ | X |
| Smoothness | □ | Δ | X |
| Quantitiy of crosslinked particles adhering to the hair, number of particles | ∞ | 1 | 0 |

These examples demonstrate the beneficial effects in using cosmetic raw materials according to the invention in which silicone or organic oils and crosslinked particles are uniformly distributed in cosmetics. The cosmetics benefit in that they can consist of such cosmetic raw materials in addition to various other types of cosmetic raw materials, in combination with such uniformly distributed silicone or organic oils and crosslinked particles. As a result, the feel on fingers and skin, the spreading of cosmetics, and the feel of cosmetics during use are improved. Such compositions are also capable of taming unruly hair, stray hair, and tangled hair. Hair is easy to arrange using such compositions the compositions impart dry feel without being sticky. Methods of making cosmetics are accordingly made more efficient.

Other variations may be made in compounds, compositions, and methods described herein without departing from the essential features of the invention. The embodiments of the invention specifically illustrated herein are exemplary only and not intended as limitations on their scope except as defined in the appended claims.

What is claimed is:

1. A method of treating hair or skin comprising applying to hair or skin an emulsion of crosslinked silicone particles contained in drops of silicone oil or organic oil, with the drops of oil containing the crossslinked silicone particles being in turn dispersed in water, the crosslinked silicone particles having an average diameter of 0.05–100 μm as determined from 10 particle size measurements with an electron microscope, and the drops of oil having an average diameter of 0.1–500 μm as determined with a laser diffraction particle size distribution device using a value corresponding to a 50 percent cumulative distribution as the size, the emulsion being prepared by a process comprising (i) dispersing in water using a surface active agent, a liquid crosslinkable composition comprising (A) an organic compound having at least two aliphatic unsaturated bonds in its molecule, (B) a silicon containing organic compound having at least two silicon bonded hydrogen atoms in its molecule, (C) a hydrosilylation reaction catalyst, a silicone oil or organic oil, and (ii) crosslinking the liquid crosslinkable composition by hydrosilylation.

2. The method according to claim 1 in which the oil has a viscosity of 1–100,000,000 mPa.s at 25° C.

3. The method according to claim 2 in which component (A) is a diene, diene oligomer, or polyether.

4. A cosmetic composition for the treatment of hair or skin comprising an emulsion of crosslinked silicone particles contained in drops of silicone oil or organic oil, with the drops of oil containing the crosslinked silicone particles being in turn dispersed in water, the crosslinked silicone particles having an average diameter of 0.05–100 μm as determined from 10 particle size measurements with an electron microscope, and the drops of oil having an average diameter of 0.1–500 μm as determined with a laser diffraction particle size distribution device using a value corresponding to a 50 percent cumulative distribution as the size, the emulsion being prepared by a process comprising (i) dispersing in water using a surface active agent, a liquid crosslinkable composition comprising (A) an organic compound having at least two aliphatic unsaturated bonds in its molecule, (B) a silicon containing organic compound having at least two silicon bonded hydrogen atoms in its molecule, (C) a hydrosilylation reaction catalyst, a silicone oil or organic oil, and (ii) crosslinking the liquid crosslinkable composition by hydrosilylation; the cosmetic composition further containing one or more other cosmetic raw materials selected from the group consisting of oils, fats, waxes, hydrocarbons, fatty acids, sterols, hormones, vitamins, fatty acid esters, moisturizers, surfactants, pigments, viscosity modifying agents, film forming agents, ultraviolet light absorbing agents, antifungal agents, anti-inflammatory agents, antiperspirants, preservatives, and fragrances.

5. A cosmetic composition according to claim 4 in which the cosmetic is an emulsion cosmetic, a crème cosmetic, a water based cosmetic, a rouge cosmetic, a foundation cosmetic, a shampoo cosmetic, or a rinse cosmetic.

6. A cosmetic composition according to claim 4 in which the oil has a viscosity of 1–100,000,000 mPa.s at 25° C.

* * * * *